United States Patent
Qiao et al.

(10) Patent No.: US 11,517,268 B2
(45) Date of Patent: Dec. 6, 2022

(54) METHOD AND DEVICE FOR DETECTING PREMATURE VENTRICULAR CONTRACTIONS BASED ON BEAT DISTRIBUTION CHARACTERISTICS

(71) Applicant: PACESETTER, INC., Sylmar, CA (US)

(72) Inventors: Yun Qiao, Valencia, CA (US); Fujian Qu, San Jose, CA (US); Stuart Rosenbeg, Woodbury, MN (US)

(73) Assignee: PACESETTER, INC., Sylmar, CA (US)

(*) Notice: Subject to any disclaimer, the term of this patent is extended or adjusted under 35 U.S.C. 154(b) by 357 days.

(21) Appl. No.: 16/262,645

(22) Filed: Jan. 30, 2019

(65) Prior Publication Data

US 2020/0237314 A1     Jul. 30, 2020

(51) Int. Cl.
  *A61B 5/00*     (2006.01)
  *A61B 5/283*    (2021.01)
  *A61B 5/364*    (2021.01)

(52) U.S. Cl.
  CPC .......... *A61B 5/7221* (2013.01); *A61B 5/283* (2021.01); *A61B 5/364* (2021.01)

(58) Field of Classification Search
  CPC ...................................................... A61B 5/04
  See application file for complete search history.

(56) References Cited

U.S. PATENT DOCUMENTS

| 7,623,911 B2 | 11/2009 | Sarkar et al. |
| 8,977,350 B2 | 3/2015 | Sarkar et al. |
| 2006/0247548 A1* | 11/2006 | Sarkar .................. A61B 5/0464 600/515 |
| 2012/0101541 A1* | 4/2012 | Corbucci ............... A61N 1/395 607/17 |
| 2012/0197148 A1* | 8/2012 | Levitan ................ A61B 5/0452 600/515 |
| 2014/0330134 A1* | 11/2014 | Chon .................. A61B 5/6898 600/479 |
| 2015/0164349 A1* | 6/2015 | Gopalakrishnan ...... G06F 19/00 600/508 |
| 2018/0192902 A1* | 7/2018 | Perschbacher ....... A61B 5/0031 |

* cited by examiner

*Primary Examiner* — Lynsey C Eiseman
(74) *Attorney, Agent, or Firm* — The Small Patent Law Group LLC; Dean D. Small

(57) ABSTRACT

A computer implemented method and system for detecting premature ventricular contractions (PVCs) are provided. The method is under control of one or more processors configured with specific executable instructions. The method obtains a cycle length (CL) distribution metric that plots a series of cardiac beats into one of a set of transition types based on R-R interval (RRI) difference pairs associated with the cardiac beats. The CL distribution metric plots the cardiac beats based on a comparison between combinations of the RRI difference pairs for corresponding combinations of the cardiac beats. The method calculates a distribution characteristic for the cardiac beats, from the series of cardiac beats that exhibit a first transition type from the set of transition types and calculates a discrimination score based on the distribution characteristic of the cardiac beats across the CL distribution metric. The method designates the CA signals to include a predetermined level of PVC burden based on the discrimination score.

18 Claims, 9 Drawing Sheets

METHOD AND DEVICE FOR DETECTING PREMATURE VENTRICULAR CONTRACTIONS BASED ON BEAT DISTRIBUTION CHARACTERISTICS

BACKGROUND

Embodiments of the present disclosure generally relate to methods and devices for methods and systems for detecting premature ventricular contractions based on distribution characteristics for cardiac beats plotted on a cycle length distribution metric.

Today, numerous atrial fibrillation (AF) detection processes are implemented within implantable cardiac monitors (ICMs) that detect atrial fibrillation based on irregularities and variation patterns in R-wave to R-wave (RR) intervals. The AF detection process steps beat by beat through cardiac activity (CA) signals and analyzes the RR intervals over a period of time. An AF episode is declared when the RR interval pattern for the suspect beat segments is sufficiently irregular and dissimilar from RR interval patterns for sinus beat segments.

However, AF detection processes may declare false AF episodes, even though a patient is not experiencing AF. False AF detection may arise due to various conditions and behavior of the heart, such as when a patient experiences frequent premature ventricular contractions (PVCs). To an extent, false AF detection is due, in part, to dependence of the AF detection process upon identification of R-wave features, with little or no input concerning other features of a cardiac event. PVCs, in general, introduce unstable RR intervals, such as short-long RR intervals, where the instability may give rise to erroneous declaration of an AF episode. Thus, PVCs present a substantial challenge in connection with AF detection algorithms that rely on RR interval variability.

Implantable cardiac devices (ICDs) without direct atrial sensing capability can detect atrial fibrillation based on R-R interval variabilities. However, frequent PVCs may cause sufficient R-R interval irregularities to trigger false AF detection. The potential to declare false AF detection may be more severe in single chamber ICDs than ICMs because PVCs occur more frequently patients who have received an ICD. In single chamber ICDs, the existing morphology discrimination algorithm can distinguish PVC cardiac beats from regular conducted cardiac beats. However, the morphology discrimination algorithm is computationally expensive and may only be used as a discriminator when VT/VF has been indicated by the rate criteria.

A conventional AF detection algorithm has been proposed that utilizes a Lorenz scatter plot to identify patterns in RRI differences. However, the conventional AF detection algorithm experiences certain limitations. The conventional AF detection algorithm does not directly calculate cluster density on the Lorenz scatter plot. Instead, it divides the plot into bins and infers a density of a cluster on the plot by subtracting a number of points on the plot by a number of occupied bins. A drawback of the conventional AF detection is that the number of points on the plot and the number of bins used to construct the Lorenz scatter plot may change the outcome significantly. The conventional AF detection algorithm does not account for heart rate (HR) and heart rate variability (HRV) differences in patients.

A need remains for methods and devices that detect the presence of frequent PVCs and that can reduce false AF detections in both ICM and single-chamber ICD devices, as well as provide important diagnostic information regarding PVC burden.

SUMMARY

In accordance with embodiments herein, a computer implemented method for detecting premature ventricular contractions (PVCs) is provided. The method is under control of one or more processors configured with specific executable instructions. The method obtains a cycle length (CL) distribution metric that plots a series of cardiac beats into one of a set of transition types based on R-R interval (RRI) difference pairs associated with the cardiac beats. The CL distribution metric plots the cardiac beats based on a comparison between combinations of the RRI difference pairs for corresponding combinations of the cardiac beats. The method calculates a distribution characteristic for the cardiac beats, from the series of cardiac beats that exhibit a first transition type from the set of transition types and calculates a discrimination score based on the distribution characteristic of the cardiac beats across the CL distribution metric. The method designates the CA signals to include a predetermined level of PVC burden based on the discrimination score.

Optionally, the method may build the CL distribution metric by obtaining cardiac activity (CA) signals for a series of cardiac beats. The method may determine ventricular cycle lengths (CL) for the series of cardiac beats from the CA signals and may determine difference combinations between consecutive CLs for corresponding sets of the cardiac beats. The method may plot the comparison between the combinations of the RRI difference pairs onto a Lorentz plot coordinate system. The CL distribution metric may plot, along a first axis, the differences between consecutive RR intervals for a set of cardiac beats, and may plot, along a second axis, differences between consecutive RR intervals for a subsequent set of cardiac beats.

Optionally, the calculating may further comprise calculating normalization for the distribution characteristic of the cardiac beats exhibiting the first transition type. The first transition type may represent long-short ARM transitions and the distribution characteristic may correspond to variance of the cardiac beats exhibiting the long-short ARM transitions. The normalization may represent normalization between the variance of the cardiac beats exhibiting the long-short ARM transitions and a variance of at least a portion of the cardiac beats may be associated with one or more of the transition types from the set of transition types.

Optionally, the CL distribution metric may represent a Lorentz plot of the cardiac beats. The method may further comprise normalizing the distribution characteristic for the cardiac beats that exhibit the first transition type by calculating a normalization represents a normalization between i) a variance of the cardiac beats in quadrant IV in the Lorentz plot and ii) a variance of cardiac beats in quadrants NV in the Lorentz plot. The discrimination score may be calculated based on the normalization. The calculating the discrimination score may comprise determining a first relation between: i) a second relation between the cardiac beats exhibiting the first transition type and cardiac beats exhibiting a second transition type from the set of transition types; and ii) the distribution characteristic for the cardiac beats exhibiting the first transition type.

Optionally, the calculating may further comprise calculating the second relation by calculating a second ratio of a number of cardiac beats exhibiting the first transition type and a number of cardiac beats exhibiting the second transition type. The first relation may represent a first ratio between the first ratio and a normalization of the distribution characteristic. The method may calculate and save the PVC burden for multiple sets of cardiac beats.

In accordance with embodiments herein, a system for detecting premature ventricular contractions (PVCs) is provided. The system comprises memory to store cardiac activity (CA) for a series of cardiac beats and a cycle length (CL) distribution metric that plots a series of cardiac beats into one of a set of transition types based on R-R interval (RRI) difference pairs associated with the cardiac beats. The CL distribution metric plots the cardiac beats based on a comparison between combinations of the RRI difference pairs for corresponding combinations of the cardiac beats. One or more processors are provided that when executing the program instructions are configured to calculate a distribution characteristic for the cardiac beats, from the series of cardiac beats, that exhibit a first transition type from the set of transition types, calculate a discrimination score based on the distribution characteristic of the cardiac beats across the CL distribution metric and designate the CA signals to include a predetermined level of PVC burden based on the discrimination score.

Optionally, the one or more processors may be further configured to build the CL distribution metric by obtaining cardiac activity (CA) signals for a series of cardiac beats. The processors may determine ventricular cycle lengths (CL) for the series of cardiac beats from the CA signals and may determine difference combinations between consecutive CLs for corresponding sets of the cardiac beats. The processors may plot the comparison between the combinations of the RRI difference pairs onto a Lorentz plot coordinate system. The CL distribution metric may plot, along a first axis, the differences between consecutive RR intervals for a set of cardiac beats, and may plots, along a second axis, differences between consecutive RR intervals for a subsequent set of cardiac beats.

Optionally, the one or more processors may be further configured to calculate a normalization for the distribution characteristic of the cardiac beats exhibiting the first transition type. The first transition type may represent long-short ARM transitions and the distribution characteristic may correspond to variance of the cardiac beats exhibiting the long-short ΔRRI transitions. The normalization may represent normalization between the variance of the cardiac beats exhibiting the long-short ΔRRI transitions and a variance of at least a portion of the cardiac beats may be associated with one or more of the transition types from the set of transition types.

The CL distribution metric may represent a Lorentz plot of the cardiac beats. The method may further comprise normalizing the distribution characteristic for the cardiac beats that may exhibit the first transition type by calculating a normalization represents a normalization between i) a variance of the cardiac beats in quadrant IV in the Lorentz plot and ii) a variance of cardiac beats in quadrants I-IV in the Lorentz plot. The discrimination score may be calculated based on the normalization. The one or more processors may be configured to calculate the discrimination score by determining a first relation between: i) a second relation between the cardiac beats exhibiting the first transition type and cardiac beats exhibiting a second transition type from the set of transition types; and ii) the distribution characteristic for the cardiac beats exhibiting the first transition type.

Optionally, the one or more processors may be configured to calculate the second relation by calculating a second ratio of a number of cardiac beats exhibiting the first transition type and a number of cardiac beats exhibiting the second transition type. The first relation may represent a first ratio between the first ratio and a normalization of the distribution characteristic. The one or more processors may be housed within at least one of an implantable medical device, an implantable cardiac monitor, a local external device, or a remote server.

DETAILED DESCRIPTION

Figure 1:
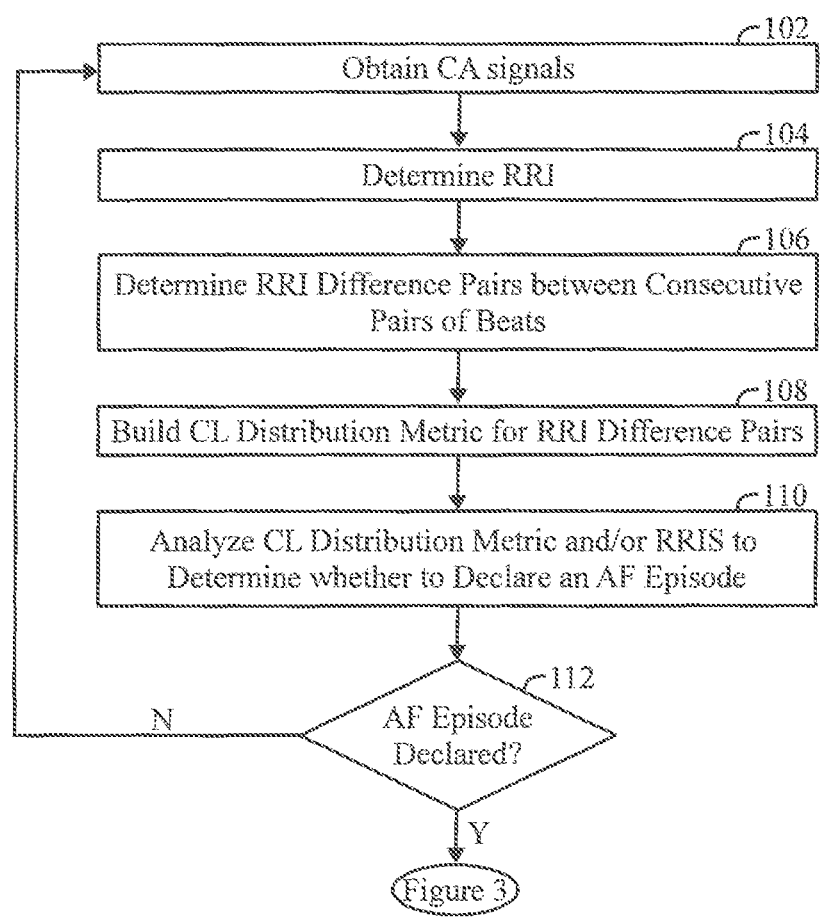
FIG. 1 illustrates a process for building a relation between ventricular cycle links (VCLs), also referred to as RR intervals (RRIs), in accordance with embodiments herein.

It will be readily understood that the components of the embodiments as generally described and illustrated in the Figures herein, may be arranged and designed in a wide variety of different configurations in addition to the described example embodiments. Thus, the following more detailed description of the example embodiments, as represented in the Figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The methods described herein may employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods may be used, in accordance with an embodiment herein. Further, wherein indicated, the methods may be fully or partially implemented by one or more processors of one or more devices or systems. While the operations of some methods may be described as performed by the processor(s) of one device, additionally, some or all of such operations may be performed by the processor(s) of another device described herein.

TERMS AND ABBREVIATIONS

The terms "cardiac activity signal", "cardiac activity signals", "CA signal" and "CA signals" (collectively "CA signals") are used interchangeably throughout to refer to an analog or digital electrical signal recorded by two or more electrodes positioned subcutaneous or cutaneous, where the electrical signals are indicative of cardiac electrical activity. The cardiac activity may be normal/healthy or abnormal/arrhythmic. Nonlimiting examples of CA signals include ECG signals collected by cutaneous electrodes, and EGM signals collected by subcutaneous electrodes.

The terms "cardiac activity data set" and "CA data set" (collectively "CA data set") are used interchangeably to refer to a data set that includes measured CA signals for a series of cardiac events in combination with device documented markers.

The terms "normal" and "sinus" are used to refer to events, features, and characteristics of, or appropriate to, a hearts healthy or normal functioning.

The terms "abnormal," or "arrhythmic" are used to refer to events, features, and characteristics of, or appropriate to, a un-healthy or abnormal functioning of the heart.

The term "real-time" refers to a time frame contemporaneous with a normal or abnormal episode occurrences. For example, a real-time process or operation would occur during or immediately after (e.g., within minutes or seconds after) a cardiac event, a series of cardiac events, an arrhythmia episode, and the like.

The term "obtain" or "obtaining", as used in connection with data, signals, information and the like, includes at least one of i) accessing memory of an external device or remote server where the data, signals, information, etc. are stored, ii) receiving the data, signals, information, etc. over a wireless communications link between the IMD and a local external device, and/or iii) receiving the data, signals, information, etc. at a remote server over a network connection. The obtaining operation, when from the perspective of an IMD, may Include sensing new signals in real time, and/or accessing memory to read stored data, signals, information, etc. from memory within the IMD. The obtaining operation, when from the perspective of a local external device, includes receiving the data, signals, information, etc. at a transceiver of the local external device where the data, signals, information, etc. are transmitted from an IMD and/or a remote server. The obtaining operation may be from the perspective of a remote server, such as when receiving the data, signals, information, etc. at a network interface from a local external device and/or directly from an IMD. The remote server may also obtain the data, signals, information, etc. from local memory and/or from other memory, such as within a cloud storage environment and/or from the memory of a workstation or clinician external programmer.

The terms "leading" and "lagging", when used in connection with describing ventricular cycle links and/or RR intervals, are used relative to a present or reference heat. By way of example, a lagging RRI or lagging RRI corresponds to the RRI or RRI between a present/reference beat and an immediately prior beat, while a leading RRI or leading RRI corresponds to the RRI or RRI between a present/reference beat and a next successive beat.

The term "RRI difference" refers to a difference between first and second R-R intervals. Each of the R-R intervals may be based on a single R-R interval between two consecutive cardiac beats (e.g., and RRI between beat 1 and beat 2). Optionally, each of the R-R intervals may be based on an average or other mathematical combination of first and second sets of R-R intervals. For example, a first RRI may be calculated from 4 cardiac beats (e.g., an average of RRIs between cardiac beats 1 and 2, cardiac beats 2 and 3, and cardiac beats 3 and 4). A second RRI may be calculated for a second set of 4 cardiac beats (e.g., an average of RRIs for cardiac beats 4-5, cardiac beats 5-6 and cardiac beats 6-7).

The term "short-short", when used in connection with describing RRI difference pairs refers to a series of cardiac beats that exhibit a particular relation between the RRI, respectively. For example, a short-short RRI difference pair corresponds to a series of cardiac beats that exhibit a short ventricular cycle length between a first set of one or more cardiac beats and a second set of one or more cardiac beats, followed by a short ventricular cycle length between a third set of one or more cardiac beats and a fourth set of one or more cardiac beats. As another example, a short-long RRI difference pair corresponds to a series of cardiac beats that exhibit a short RRI between a first set of one or more cardiac beats and a second set of one or more cardiac beats, followed by a long RRI between a third set of one or more cardiac beats and a fourth set of one or more cardiac beats. As another example, a long-short RRI difference pair corresponds to a series of cardiac beats that exhibit a long RRI between a first set of one or more cardiac beats and a second set of one or more cardiac beats, followed by a short RRI between a third set of one or more cardiac beats and a fourth set of one or more cardiac beats. As another example, a long-long RRI difference pair corresponds to a series of cardiac beats that exhibit a long RRI between a first set of one or more cardiac beats and a second set of one or more cardiac beats, followed by a long RRI between a third set of one or more cardiac beats and a fourth set of one or more cardiac beats. As a further example, each RRI difference pair may be calculated from 4 cardiac beats. For example, in a short-short RR difference pair, the first "short" $\Delta$RRI indicates that the RRI between cardiac beats 2 and 3 is shorter than the RRI between cardiac beats 1 and 2. The second "short" $\Delta$RRI indicates that RRI between cardiac beats 3 and 4 is shorter than the RRI between cardiac beats 2 and 3. In other words, the terms "short" and "long" indicate negative and positive $\Delta$RRIs, respectively. Accordingly, rather than describing the value of an RRI between 2 cardiac beats, the terms "short" and "long" describe the changes in two consecutive RRIs.

Embodiments may be implemented in connection with one or more implantable medical devices (MDs). Nonlimiting examples of IMDs include one or more of neurostimulator devices, implantable leadless monitoring and/or therapy devices, and/or alternative implantable medical devices. For example, the MD may represent a cardiac monitoring device, pacemaker, cardioverter, cardiac rhythm management device, defibrillator, neurostimulator, leadless monitoring device, leadless pacemaker and the like. For example, the IMD may include one or more structural and/or functional aspects of the device(s) described in U.S. Pat. No. 9,333,351 "Neurostimulation Method And System To Treat Apnea" and U.S. Pat. No. 9,044,810 "System And Methods For Providing A Distributed Virtual Stimulation Cathode For Use With An Implantable Neurostimulation System", which are hereby incorporated by reference. Additionally or alternatively, the IMD may include one or more structural and/or functional aspects of the device(s) described in U.S. Pat. No. 9,216,285 "Leadless implantable Medical Device Having Removable And Fixed Components" and U.S. Pat. No. 8,831,747 "Leadless Neurostimulation Device And Method Including The Same", which are hereby incorporated by reference. Additionally or alternatively, the IMD may it one or more structural and/or functional aspects of the device(s) described in U.S. Pat. No. 8,391,980 "Method And System For Identifying A Potential Lead Failure In An Implantable Medical Device" and U.S. Pat. No. 9,232,485 "System And Method For Selectively Communicating With An Implantable Medical Device", which are hereby incorporated by reference.

Additionally or alternatively, the IMD may be a subcutaneous IMD that includes one or more structural and/or functional aspects of the device(s) described in U.S. application Ser. No. 15/973,195, titled "Subcutaneous Implantation Medical Device With Multiple Parasternal-Anterior Electrodes" and filed May 7, 2018; U.S. application Ser. No. 15/973,219, titled "Implantable Medical Systems And Methods Including Pulse Generators And Leads" filed May 7, 2018; U.S. application Ser. No. 15/973,249, titled "Single Site Implantation Methods For Medical Devices Having Multiple Leads", filed May 7, 2018, which are hereby incorporated by reference in their entireties. Further, one or more combinations of IMDs may be utilized from the above incorporated patents and applications in accordance with embodiments herein.

Additionally or alternatively, the IMD may be an implantable cardiac monitor (ICM) that includes one or more structural and/or functional aspects of the ICMs described in:
  U.S. patent application Ser. No. 15/973,351, titled "METHOD AND SYSTEM TO DETECT R-WAVES IN CARDIAC ARRHYTHMIC PATTERNS",
  U.S. patent application Ser. No. 16/007,878, titled "METHOD AND SYSTEM TO DETECT R-WAVES IN CARDIAC ACTIVITY SIGNALS",
  U.S. patent application Ser. No. 15/973,384, titled "METHOD AND SYSTEM TO DETECT NOISE IN CARDIAC ARRHYTHMIC PATTERNS",
  U.S. patent application Ser. No. 15/973,307, titled "METHOD AND SYSTEM TO DETECT POST VENTRICULAR CONTRACTIONS IN CARDIAC ARRHYTHMIC PATTERNS".

The complete subject matter of the foregoing applications is expressly incorporated by reference in their entireties.

In accordance with embodiments herein, methods and systems are described that utilize a R-R interval based PVC identification process that can be used in various types of IMDs, including but not limited to ICMs and single-chamber ICDs, to reduce false AF detection due to frequent PVCs and to provide PVC burden diagnostic information. The PVC identification processes herein calculate differences in duration between consecutive R-R intervals ($\Delta$RRI) and utilize the differences to construct a Lorenz scatter plot of ARM. The PVC identification processes then utilize the Lorenz scatter plot to compute a discrimination score based on 1) a ratio of a number of points in quadrant IV (Q4) and quadrant I (Q1) of the Lorenz scatter plot and 2) a variance of Q4 points relative (e.g., normalized) to a variance of all points on the Lorenz scatter plot. The variance of Q4 cardiac beats is normalized to account for differences in heart rate and heart rate variability of individual patients.

In accordance with embodiments herein, the PVC identification process utilizes a relatively simple series of mathematical operations that can run on a continuous basis (e.g., every 1-5 minutes) to provide PVC burden diagnostic information in addition to reducing false AF detection. The ability to continuously monitor PVC burden in an IMD (e.g., ICM and single-chamber devices) is potentially beneficial to the clinicians and patients as PVCs are associated with reduced quality of life, increased outpatient visits, and increased risk of sudden cardiac death.

FIG. 1 illustrates a process for building a relation between ventricular cycle links (Vas), also referred to as RR intervals (RRIs). In accordance with embodiments herein. The process of FIG. 1 may be implemented by one or more processors of an IMD in real time on a periodic basis. Optionally, the process of FIG. 1 may be implemented by one or more processors of a local external device that may receive signals indicative of cardiac events over a series of cardiac beats, such as when a local external device obtains cardiac signals from an IMD periodically over the course of the day and/or on a nightly basis. Optionally, the process of FIG. 1 may be implemented by one or more processors of a remote server that received signals indicative of cardiac events over a series of events, such as when the remote server obtains previously recorded cardiac signals from an IMD (and/or local external device).

At 102, the one or more processors obtain cardiac activity (CA) signals for a series of cardiac beats for a select period of time. For example, the cardiac events may be collected by an IMD for a select number of seconds or minutes, a select number of cardiac beats, and the like, and then processed by the IMD, and/or to limit or to a local external device for processing, and/or to limit or to a remote server for processing. At 104, the one or more processors determine ventricular cycle lengths (VCLs), also referred to as RR intervals (RRIs), for the series of cardiac beats from the CA signals. At 106, the one or more processors determine RRI difference pairs between consecutive pairs of CLs for corresponding combinations of successive cardiac beats from the series of cardiac beats.

At 108, the one or more processors build a CL distribution metric for the RRI difference pairs across the series of cardiac beats. The CL distribution metric maps each of the cardiac beats into one of a set of transition types based on RRI difference pairs associated with the cardiac beats. The CL distribution metric plots the cardiac beats based on a comparison between combinations of the RRI difference pairs for corresponding combinations of the cardiac beats. By way of example, the CL distribution metric may represent a Lorenz scatter plot. The CL distribution metric plots a comparison between combinations of the RRI difference pairs for corresponding combinations of the cardiac beats. For example, the CL distribution metric plots, along a first axis, the differences between consecutive RR intervals for each beat, and plots, along a second axis, differences between consecutive RR intervals for each subsequent beat. The set of transition types may include long-long transitions (quadrant I), short-long transitions (quadrant II), short-short transitions (quadrant III) and long-short transitions (quadrant IV).

At 110, the one or more processors analyze at least one of the CL distribution metric or the RRIs to determine whether to declare an occurrence of atrial fibrillation (AF) episode. At 112, the one or more processors determine whether an AF episode has been declared. When no AF episode is declared, the process returns to 102. Alternatively, when an AF episode is declared, the process continues to FIG. 3.

Figure 2A:
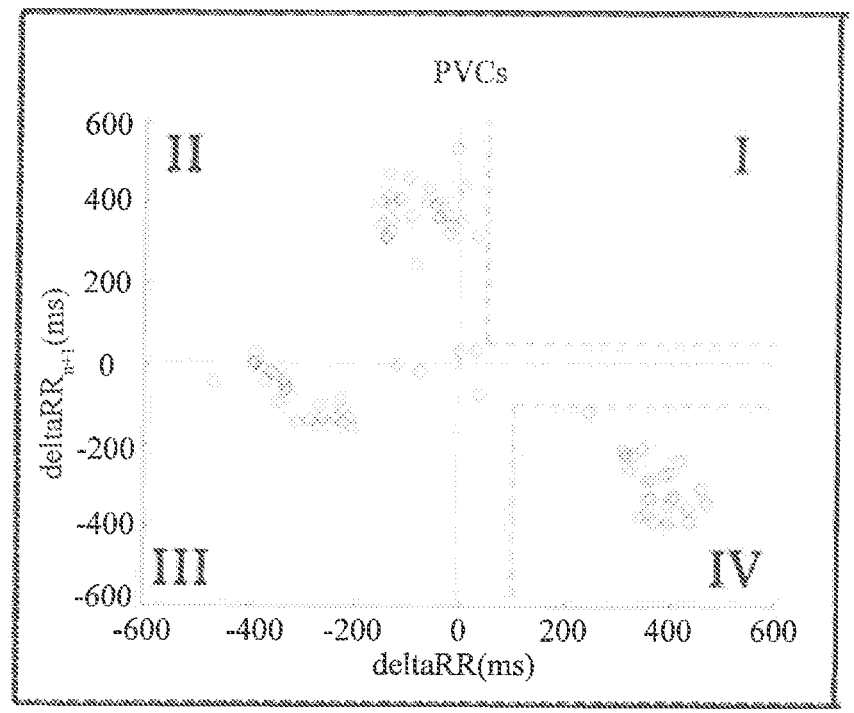
FIG. 2A illustrates a Lorenz scatter plot of RRIs for one or more patients experiencing post ventricular contractions.
Figure 2B:
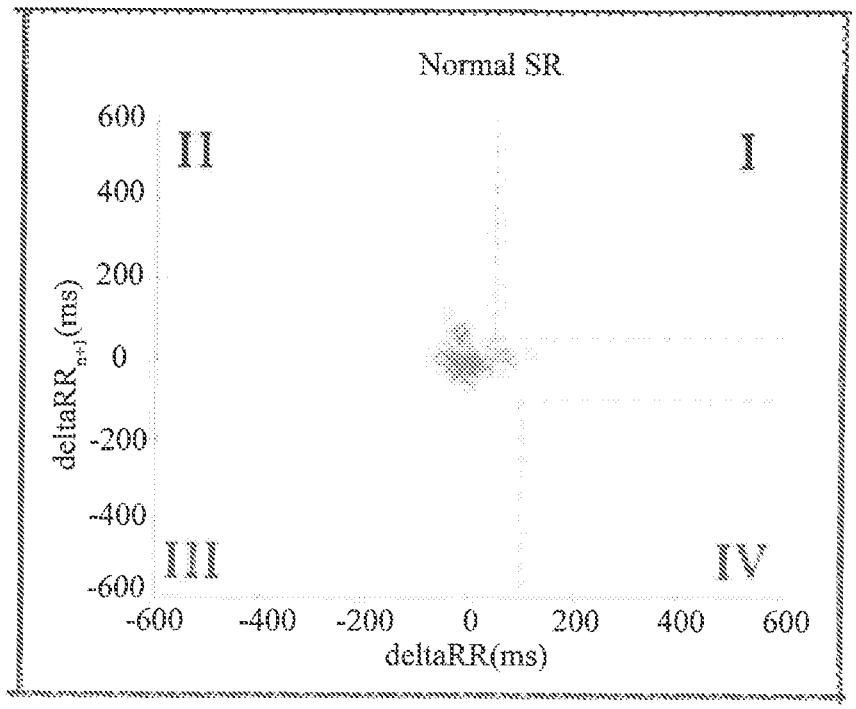
FIG. 2B illustrates a Lorenz scatter plot of RRIs for one or more patients experiencing normal sinus rhythm.
Figure 2C:
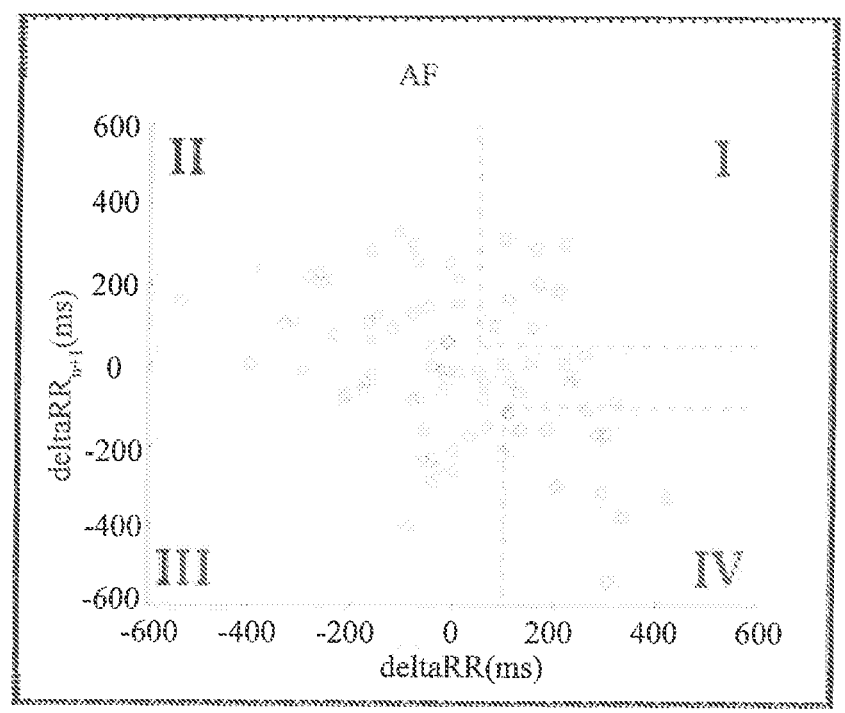
FIG. 2C illustrates a Lorenz scatter plot of RRIs of one or more patients experiencing atrial fibrillation.

FIGS. 2A-2C illustrate examples of Lorenz scatter plots of ventricular cycle length (RRI) data obtained from patients exhibiting three different physiologic behaviors. The differences between consecutive RR intervals (ΔRRs) are plotted for a time series of R-R intervals (RRIs). The Lorenz scatter plot is a Cartesian coordinate system defined by $\Delta RR_i$ along the x-axis and $\Delta RR_{i-1}$ along the y-axis. As such, each plotted point in a Lorenz scatter plot is defined by an x-coordinate equaling $\Delta RR_i$ and a y-coordinate equaling $\Delta RR_{i-1}$. The $\Delta RR_i$ is the difference between the $i^{th}$ RRI and the previous RRI, $RRI_{i-1}$. The $\Delta RRI_{i-1}$ is the difference between $RRI_{i-1}$ and the previous RRI, $RRI_{i-2}$. As such, each data point plotted on the Lorenz scatter plot represents a RRI pattern relating to three consecutive RRIs: $RRI_i$, $RRI_{i-1}$ and $RRI_{i-2}$, measured between four consecutively sensed R-waves. As noted previously, RRI information is not limited to detection of R-waves and determination of RRIs. The terms RRI and $\Delta RR_i$ as used herein refer generally to a measurement of RRI and the difference between two consecutive RRI measurements, respectively, whether the RRI measurements were derived from a series of R-wave detections from an EGM or ECG signal or another ventricular cycle event detection from any other physiological signal (e.g., a peak pressure determined from a pressure signal). For the sake of illustration, the embodiments described herein often refer to R-wave detections for performing RRI measurements and the determination of ($\Delta RR_i$, $\Delta RR_{i-1}$) points.

In FIG. 2A-2C, the Lorenz plots have units of ms. Instead of showing the absolute changes in RRI (ΔRRI=RRI2−RRI1), the plot may also be generated with relative changes in RRI (% ΔRRI=(RRI2−RRI1)/RRI1).

FIG. 2A illustrates a Lorenz scatter plot of ΔRRIs for one or more patients experiencing post ventricular contractions. FIG. 2B illustrates a Lorenz scatter plot of ΔRRIs for one or more patients experiencing normal sinus rhythm, while FIG. 2C illustrates a Lorenz scatter plot of ΔRRIs of one or more patients experiencing atrial fibrillation. When a patient has a normal sinus rhythm, the cardiac beats plotted on the Lorenz scatter plot (FIG. 2B) exhibit small variants across the quadrants. The Lorenz scatter plots present data points mapped onto a Cartesian coordinate system that is divided into four quadrants I-IV. The four quadrants correspond to different combinations of successive ΔRRIs, where the first or lagging ΔRRI is between RRI 1 and RRI 2 (e.g., a present/reference RRI and a prior RRI) and where the second or leading ΔRRI is between RRI 2 and RRI 3 (e.g., a present/reference RRI and a next RRI). In the quadrants of the Lorenz scatter plot, quadrant I plots all sets of cardiac beats that exhibit long-long RRI difference pairs, quadrant II plots all sets of cardiac beats that exhibit short-long RRI difference pairs (e.g., a short RRI between cardiac beats one and two, followed by a long RRI between cardiac beats 2 and 3), quadrant III plots all sets of cardiac beats that exhibit short-short RRI difference pairs (e.g., a short ventricular cycle length between cardiac beats 1 and 2, followed by a short ventricular cycle length between cardiac beats 2 and 3), and quadrant IV plots all sets of cardiac beats that exhibit long-short RRI difference pairs (e.g., a long ΔRRI between RRI 1 and RRI 2, followed by a short ΔRRI between RRI 2 and RRI 3).

Figure 3:
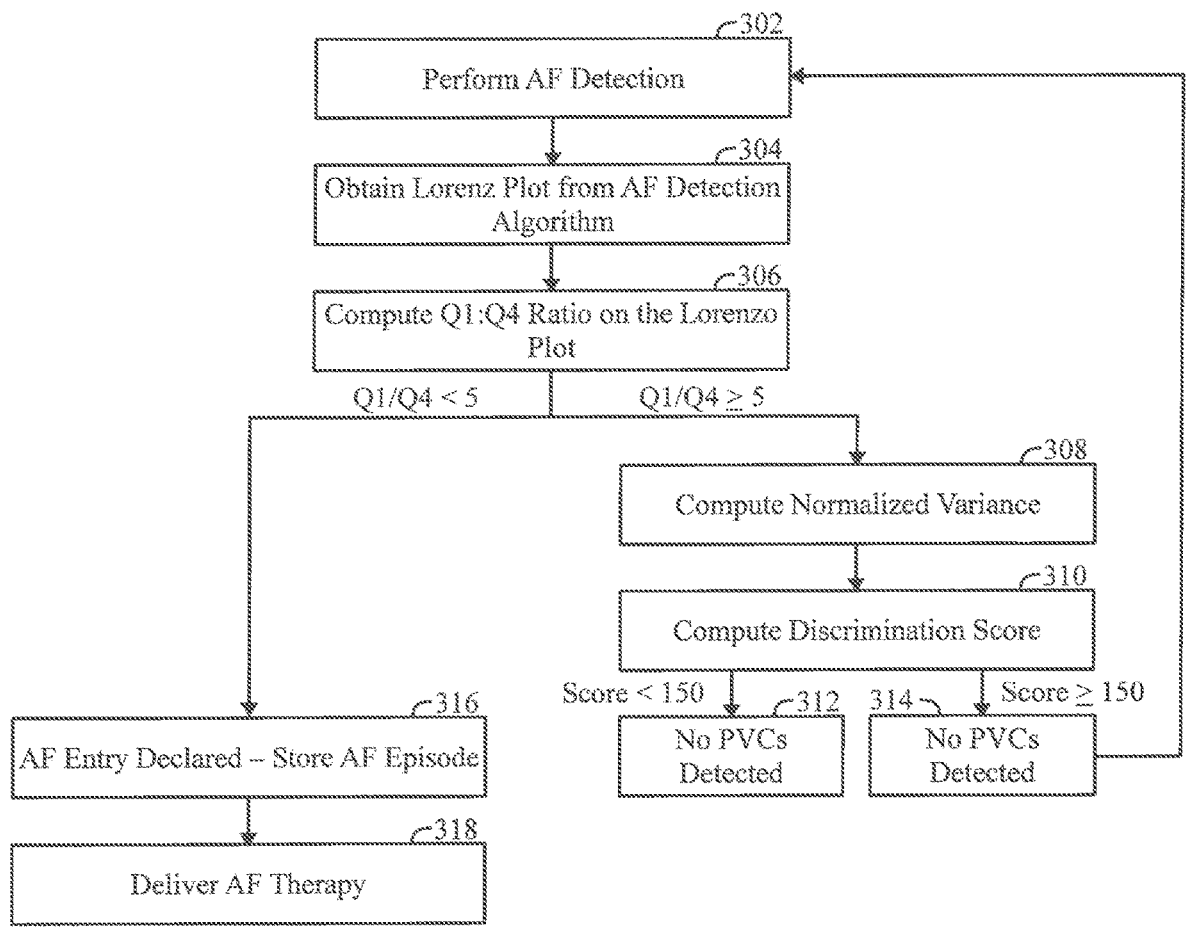
FIG. 3 illustrates a process for performing PVC discrimination in accordance with embodiments herein.

Embodiments herein utilize the Lorenz scatter plot to compare the ΔRRI of each beat with the subsequent beat. Because the PVC coupling interval and the post-PVC pause interval are governed by the refractoriness of the underlying substrate, ECG recordings with frequent PVCs exhibit distinct patterns of clustering on the Lorenz scatter plot (FIG. 2A). PVC related episodes are expected to exhibit a certain relation between the number of Q1 and Q4 ΔRRI transitions, and more specifically, exhibit relatively "tight" clustering of cardiac beats in quadrant I and quadrant IV. On the other hand, the RR intervals during AF have significant variability and little beat to beat correlation, resulting in a wide sparse distribution on the Lorenz scatter plot (FIG. 2C). When a series of cardiac beats correspond to an AF episode, the cardiac beats are not clustered in the same manner as PVC related cardiac beats. Instead, a series of cardiac beats associated with an AF episode are spread out in a more even distribution over multiple transition types, namely over the quadrants I-IV. The discrimination algorithm uses a quadrant-based method to distinguish lone PVCs, bigeminy, and trigeminy from AF. Since each PVC is followed by only one prolonged interval, Lorenz scatter plot of a ECG with PVCs would have zero to few cardiac beats in quadrant I (Q1). Therefore, calculating the ratio of the number of cardiac beats in quadrant IV (Q4) and quadrant I could be used to efficiently discriminate PVCs from most AF. To avoid counting normal sinus cardiac beats, cutoff values of 50 and 100 ms were used when counting the number of cardiac beats in quadrant I and IV respectively. The cutoff values are empirically determined. A longer cutoff value is used for Q4 because the magnitude of ΔRRI is greater in long-short ΔRRI transitions than that of long-long transitions, FIG. 3 illustrates a process for performing PVC discrimination in accordance with embodiments herein. At 302, the one or more processors perform an AF detection process that detects candidate AF episodes. The AF episodes are referred to as "candidate" AF episodes as the process of FIG. 3 seeks to verity the candidate AF episodes as valid AF episodes or declare the candidate AF episode to be a false AF episode. The AF detection process may be based on various algorithms. For example, the AF detection process may implement one or more of the AF detection algorithms described in the patents, and applications incorporated herein. Additionally or alternatively, the AF detection process may implement AF detection based on information in the CL distribution metric. The process of FIG. 3 may remain at 302, repeatedly analyzing new cardiac activity signals for new cardiac beats until an AF episode is detected. As new cardiac beats are analyzed at 302, one or more AF counting buffers are maintained, to count each beat potentially associated with an AF episode. When the count of candidate AF cardiac beats exceeds the threshold (e.g., 10 out of 15 cardiac beats or otherwise), the process declares a candidate AF episode. Alternatively, the process may move from 302 to 304 in certain cases even when no AF episode was detected at 302, such as periodically or based on certain other physiologic or non-physiologic criteria (e.g., other patterns in the cardiac activity, when the patient is laying in a prone position or exercising, at an instruction from a local external device).

At 304 the one or more processors obtain the CL distribution metric (e.g., a Lorenz scatter plot) for the RR difference pairs across the series of cardiac beats. As explained above in connection with FIG. 1, the CL distribution metric may be generated by plotting each beat on a Cartesian coordinate system as a comparison between combinations of the RRI difference pairs for corresponding combinations of cardiac beats. Next, the operations at 306-310 calculate a discrimination score based on a variability of the cardiac beats (RRI difference pairs) across the CL distribution metric.

At 306, the one or more processors calculate a relation between first and second types of ΔRRI transitions in the RRI difference pairs. For example, the calculation may determine a ratio between a number of RRI difference pairs associated with a first transition type and a number of RRI difference pairs associated with a second transition type. More specifically, the ratio may be determined between the number of RR difference pairs in the first quadrant and fourth quadrant, wherein the first quadrant corresponds to long-long ΔRRI transitions and the fourth quadrant corresponds to long-short ΔRRI transitions.

Optionally, the relation may be based on a mathematical operator other than a ratio between the number of points in the first and fourth quadrants. Additionally or alternatively, the relation may be based on information other than simply the number of points in the first and fourth quadrants. For example, the relation may be based on the number of points in the fourth quadrant and a mathematical combination of the number of points in one or more of quadrants I IV.

At 306, the one or more processors compare the relation between the first and second transition types (e.g., Q1/Q4) to a threshold and based thereon, the process branches between one of two paths. When the relation fails below the threshold (e.g., Q1/Q4<5), flow moves to 316. At 316, for potential AF episodes with a Q4/Q1 ratio of below 5, the one or more processors automatically label the AF episode as non-PVC related, PVC related episodes are expected to exhibit a certain relation between the number of Q1 and Q4 ARM transitions, and more specifically, exhibit relatively "tight" clustering of cardiac beats in quadrant I and quadrant IV. In contrast, when a series of cardiac beats correspond to an AF episode, the cardiac beats are not clustered in the same manner as PVC related cardiac beats. Instead, a series of cardiac beats associated with an AF episode are spread out in a more even distribution over multiple transition types, namely over the quadrants I-IV. In the present example, in a PVC related episode, the process expects a number of cardiac beats that exhibit long-short ΔRRI transitions (corresponding to quadrant IV) to be relatively large (e.g., at least more than ⅕) as compared to a number of cardiac beats that exhibit long-long ΔRRI transitions (corresponding to quadrant I). When the foregoing relation does not occur over a series of cardiac beats, the process is able to classify the episode as a non-PVC related episode. Thus, at 316, the process declares an AF entry or more specifically confirms a candidate AF entry. At 316, the one or more processors store the AF episode, which may include storing information describing the AF episode (e.g., a duration, number of cardiac beats, entry and exit times). Optionally, the processors may store the cardiac activity signals for all or a portion of the AF episode. The stored information is then made available for telemetry from the IMD to a local external device and a remote server.

Optionally, flow may move from 316 to 318. At 318, the IMD may deliver an AF therapy configured to terminate the AF episode. Optionally, the operation at 318 may be omitted entirely, such as when the IMD represents an implantable cardiac monitoring device that does not include the capability to deliver AF therapy. Optionally, the operation at 318 may include, or be limited to, transmitting a notification that an AF episode is occurring, to a local external device. In response to which, the local external device may direct the patient to perform a desired action, such as taking medication, laying down, contacting medical personnel and the like.

Returning to 306, when the relation equals or exceeds the threshold (e.g., Q1/Q4≥5), flow moves to 308. When flow moves from 306-308, the process is determined that the candidate AF episode is exhibiting a relation between the number of quadrant I and quadrant IV ΔRRI transitions that is indicative of a PVC related behavior. At 308, the one or more processors compute a normalization for a distribution characteristic for cardiac beats exhibiting a transition type of interest. In connection there with, the one or more processors calculate a distribution characteristic for cardiac beats exhibiting a transition type of interest and then calculate a normalization for the distribution characteristic. The distribution characteristic may also be referred to as a beat distribution characteristic and/or transition distribution characteristic. For example, the transition type of interest may represent long-short ΔRRI transitions (quadrant IV), while the distribution characteristic may correspond to variance. Variance represents a measure of an extent to which the data (e.g., cardiac beats) are spread across a map. Optionally, the distribution characteristic may correspond to a standard deviation or other mathematical relation of the manner in which the cardiac beats are spread across quadrant IV and/or another quadrant within the Lorenz scatter plot. Accordingly, in the present example, the one or more processors compute a normalized transition distribution. The normalization of the transition distribution (e.g., transition variance) adjusts the values indicative of the distribution measured over different scales to a common scale, thereby accounting for differences in heart rate distribution (e.g., variance) over time by an individual patient, as well as differences in heart rate distributions (e.g., variances) between patients. The normalized distribution (e.g., transition variance) represents a normalization between variance in a first transition type of interest and at least one other transition type of interest. The distribution for the first transition type of interest represents the variance between cardiac beats in quadrant IV (e.g., the variance between cardiac beats associated with long-short ΔRRI transitions). The distribution for at least one other transition type of interest may correspond to the variance across all transition types or a subset of the transition types. For example, the transition variance in the cardiac beats in quadrant IV may be normalized with respect to a transition variance of the cardiac beats in all 4 quadrants, namely a total set of cardiac beats independent of a type of ΔRRI transition. Additionally or alternatively, the transition variance of the cardiac beats in quadrant IV may be normalized with respect to a transition variance of a subset of the cardiac beats distributed across all 4 quadrants, such as a select portion of the total set of cardiac beats independent of a type of ΔRRI transition. Additionally or alternatively, the transition variance of the cardiac beats in quadrant IV may be normalized with respect to a transition variance of the cardiac beats in a subset of the quadrants, such as normalizing the quadrant IV variance with respect to the quadrant I variance, quadrant II variance, quadrant III variance, or any combination thereof. In the example of FIGS. 1-3, the normalization may represent a normalization between i) a variance of the cardiac beats in quadrant IV in the Lorentz plot and ii) a variance of cardiac beats in quadrants I-IV in the Lorentz plot.

At 310, the one or more processors compute a discrimination score based at least on the distribution characteristic of the cardiac beats that exhibit the transition type of interest across the CL distribution metric. The discrimination score may be determined based on a ratio of the relation determined at 306 and the normalized distribution characteristic determined at 308. In accordance with at least some embodiments, the discrimination score is obtained by dividing the ratio of Q4 to Q1 cardiac beats by the normalized Q4 variance. By way of example, the discrimination score may be calculated based on the following equation.

$$\text{Discrimination score} = \frac{\left(\frac{\text{\# beats in } Q4}{\text{\# of beats in } Q1}\right)}{\left(\frac{\text{variance}(Q4 \text{ beats})}{\text{variance}(\text{all beats})}\right)} \quad \text{(Equation 1)}$$

Optionally, the denominator of equation 1 may only be computed in cases when the Q4/Q1 ratio in the numerator exceeds 5, in order to minimize the duty cycles of the discrimination algorithm. Optionally, the denominator of equation one may be computed more often, such as each time the numerator is computed.

For rare cases where AF occurs concurrently with frequent PVCs, the ratio of Q4 to Q1 cardiac beats may be similar to that of PVC only episodes. However, the clustering of Q4 cardiac beats for an AF episode is always more dispersed than that of a PVC triggered episode. Therefore, to avoid false rejection of true AF episodes with PVCs, the variance of the Q4 cardiac beats is also taken into consideration at 310. To account for patient to patient differences in HR variability, the Q4 variance is normalized to the variance of the entire Lorenz scatter plot. Additionally or alternatively, the Q4 variance may be normalized to the variance of one other quadrant in the Lorenz scatter plot and/or a combination of other quadrants in the Lorenz scatter plot.

To preserve the sensitivity of the AF detection algorithm and to maintain a select level of accuracy for the PVC discrimination algorithm, in accordance with embodiments herein, and IMD implementing the methods described herein may do so at select times and/or based on certain criteria. For example, and IMD may perform PVC discrimination at a point in an entry point for AF detection, as the time of the AF detection entry may lag an onset of an actual AF occurrence. To streamline the implementation of the PVC discrimination algorithm in device firmware, PVC discrimination may be performed when the criteria for AF entry in an AF detection algorithm is met. When a PVC event is identified by the discrimination algorithm, the state of the AF detection algorithm may be reset to clear out the PVC intervals. If no PVCs are detected, the AF detection algorithm would proceed to declare AF entry and store the episode.

Once the discrimination score has been computed at 310, the one or more processors compare the discrimination score to a score threshold (e.g., 150). Based on the comparison to the discrimination score, the process branches 2 312 or 314. When the discrimination score is below the threshold, flow branches to 312. At 312, the one or more processors record an indication that no PVCs were detected. When no PVCs are detected at 312, flow moves to 316 and the one more processors declare AF entry, store the AF episode and potentially deliver an AF therapy.

Returning to 310, when the discrimination score equals or is above the score threshold, flow branches to 314. At 314, the one or more processors record indication that PVCs were detected. At 314, the one or more processors also declare the candidate AF episode to be a false AF episode. Thereafter, flow returns to 302 and the AF count buffer is reset.

Figure 4:
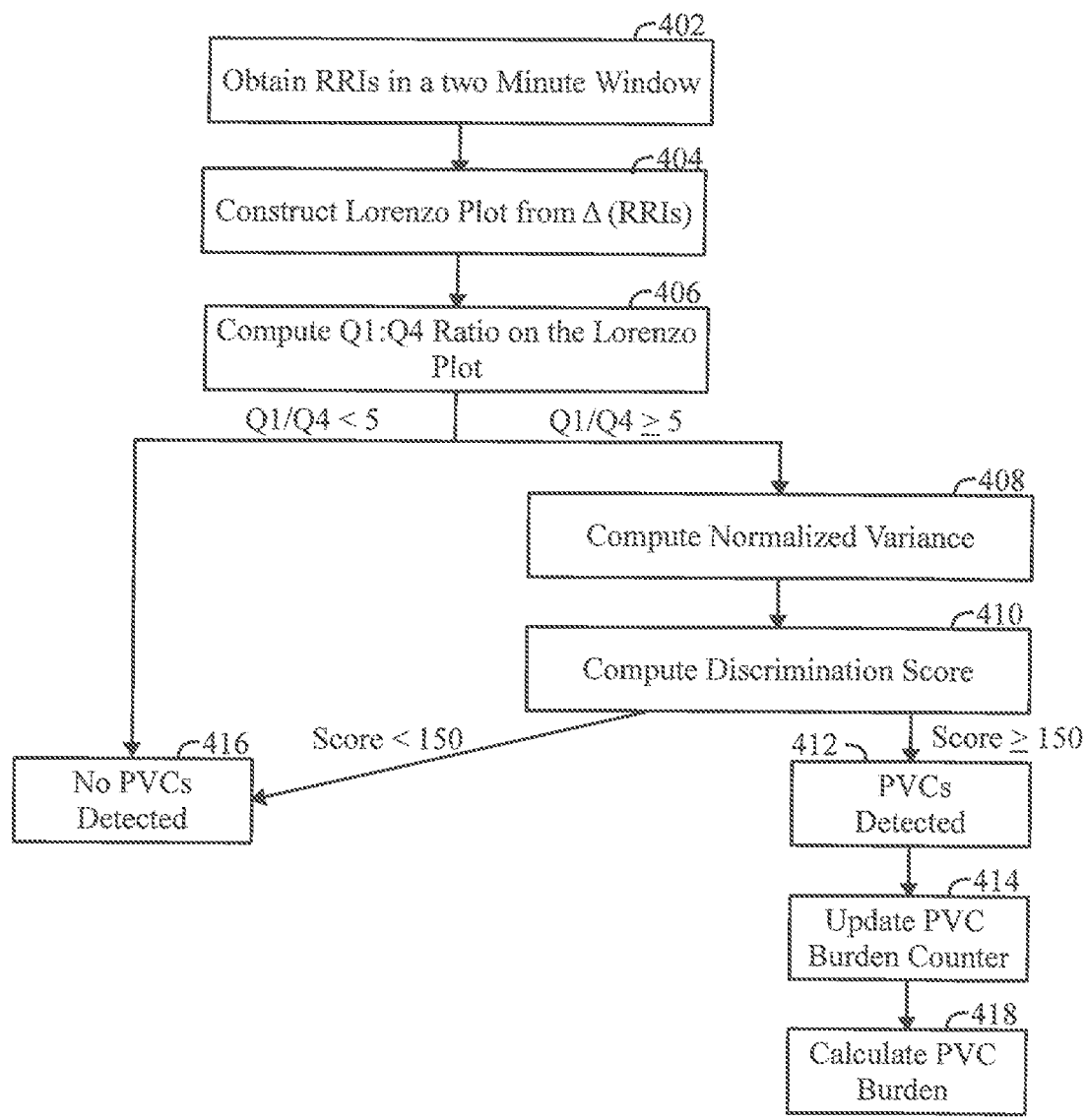
FIG. 4 illustrates a process for calculating PVC burden in accordance with embodiments herein.

FIG. 4 illustrates a process for calculating PVC burden in accordance with embodiments herein. The process of FIG. 4 may be Implemented in parallel with or independent of the process of FIG. 3. It should be recognized that the operations of FIG. 4 may be performed in connection with, or independent of and without regard for, whether an AF episode has been detected. At least a portion of the operations described in connection with FIG. 4 may correspond to similar operations in FIGS. 1 and 3, and thus are not described in as much detail. At 402, the one or more processors obtain CA signals for a predetermined window of interest (e.g., a 2 minute window). At 402, the processors also determine RRIs associated with the CA signals (e.g., as described herein in connection with 102, 104 in FIG. 1). At 404, the one or more processors determine RRI difference pairs between consecutive pairs of cardiac beats and build a CL distribution metric by plotting the cardiac beats based on the RRI difference pairs (e.g., as described in connection with 106, 108 in FIG. 1).

At 406, the one or more processors calculate a relation between first and second types of ΔRRI transitions in the RRI difference pairs (e.g., similar to the operation at 306 in FIG. 3). For example, the calculation may determine a ratio between a number of RRI difference pairs associated with a first transition type and a number of RRI difference pairs associated with a second transition type. More specifically, the ratio may be determined between the number of RRI difference pairs in the first quadrant and fourth quadrant, wherein the first quadrant corresponds to long-long ΔRRI transitions and the fourth quadrant corresponds to long-short ARM transitions. At 406, the one or more processors compare the relation between the first and second transition types (e.g., Q1/Q4) to a threshold and based thereon, the process branches between one of two paths. When the relation falls below the threshold (e.g., Q1/Q4<5), flow moves to 416. At 416, the one or more processors automatically label the series of cardiac beats to have no PVCs detected. Alternatively, when the relation equals or exceeds the threshold (e.g., Q1/Q4≥5), flow moves to 408.

When flow moves from 406-408, the process has determined that the series of cardiac beats are exhibiting a relation between the number of quadrant I and quadrant IV ΔRRI transitions that is indicative of PVC related behavior. At 408, the one or more processors compute a normalization for a distribution characteristic for cardiac beats exhibiting a transition type of interest. As explained above in connection with 308 (FIG. 3), the normalization may represent a normalization between i) a variance of the cardiac beats in quadrant IV in the Lorentz plot and ii) a variance of cardiac beats in quadrants I-IV in the Lorentz plot.

At 410, the one or more processors compute a discrimination score based at least on the distribution characteristic of the cardiac beats that exhibit the transition type of interest across the CL distribution metric. The discrimination score may be determined based on a ratio of the relation determined at 406 and the normalized distribution characteristic determined at 408. In accordance with at least some embodiments, the discrimination score is obtained by dividing the ratio of Q4 to Q1 cardiac beats by the normalized Q4 variance, such as utilizing the equation discussed above in connection with the operation at 310.

Once the discrimination score has been computed at 410, the one or more processors compare the discrimination score to a score threshold (e.g., 150). Based on the comparison to the discrimination score, the process branches to 412 or 416. When the discrimination score is below the threshold, flow branches to 416 where the series of cardiac beats are designated to contain no PVCS. When the discrimination score equals or is above the score threshold, flow branches to 412. At 412, the one or more processors record an indication that PVCs were detected in the series of cardiac beats. Next, at 414, the one or more processors update a PVC burden counter.

The operations of FIG. 4 may be run on a continuous basis to update PVC burden counters in connection with various windows of CA signals collected over time to calculate PVC burden. For example, every 2-minute (or 5 minute) block the process analyzes ΔRRIs for the cardiac beats recorded during the block and determines if PVCs are present. When PVCs are present, the set of cardiac beats will be registered as a PVC set of cardiac beats. When PVCs are not present, the set of cardiac beats will be labeled as a non-PVC set of cardiac beats.

At 418, the one or more processors calculate the PVC burden. For example, the PVC burden may be calculated as the ratio of i) the number of PVC sets of cardiac beats and the total ii) the total number of sets of cardiac beats that are analyzed over a period of time (e.g., a day, week, month, year).

Figure 5:
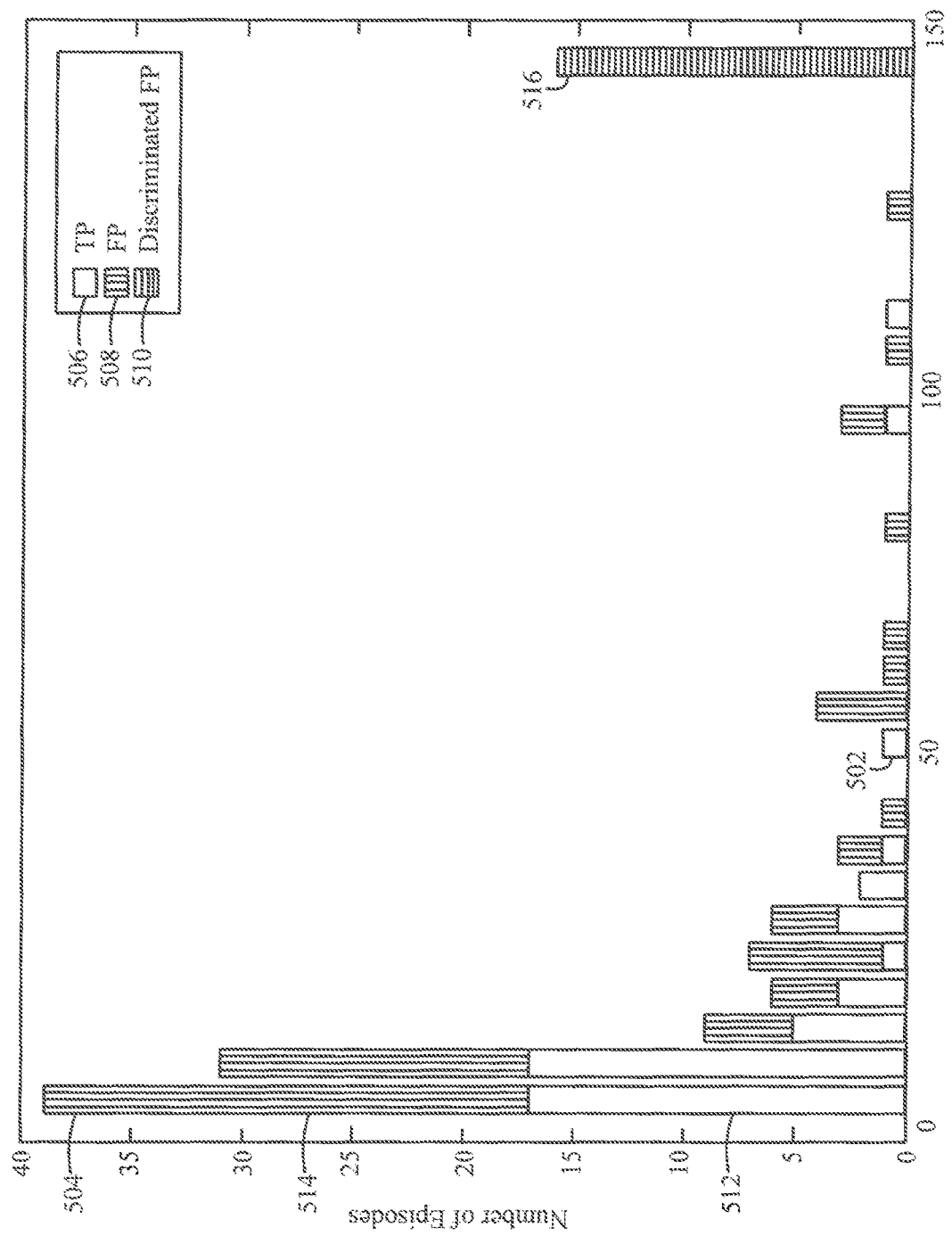
FIG. 5 illustrates an example of the manner in which PVC burden may be presented on a display.

FIG. 5 illustrates an example of the manner in which PVC burden may be presented on a display of a workstation, laptop computer, smart phone, tablet device and the like. In FIG. 5, a horizontal axis plots discrimination score, while the vertical axis plots the number of episodes that are designated to have the corresponding discrimination score. By way of example, the bar 502 indicates that approximately one episode was attributed by discrimination score of 50, while bar 504 denotes that approximately 39 episodes were assigned a discrimination score of zero.

The PVC discrimination process described herein was tested on a set of 137 cardiac activity signals (SEGM signals) collected by an implantable cardiac monitor. FIG. 5 illustrates a number of true positives 506, false positives 508 and discriminated false positives 510 identified by the discrimination process described herein. The 137 segments of SEGM signals were detected as AF by an AF detection algorithm. The segments were manually adjudicated by a panel of experts, who determined 53 of the 137 episodes as true AF (TP) and the rest of the episodes as false detections (FP). When all 137 episodes were evaluated by the PVC discrimination algorithm, 16 episodes previously adjudicated as false detections were ruled to be PVC related by the algorithm. With reference to the bar 504 (corresponding to discrimination scores of zero), approximately 17 episodes were identified as true positives (as denoted at 512), while approximately 22 episodes were identified as false positives (as denoted at 514). The episodes (bar 516) assigned to discrimination score of slightly under 150 represent discriminated false positives. From the set of cardiac activity signals, 53 of the 137 episodes were adjudicated as true positives (TPs), resulting in a positive predictive value (PPV) of 38%. Among the fake positive (FP) episodes, 80% were adjudicated as irregular sinus rhythm, while the remaining 20% were adjudicated as frequent PVCs or other/ uncertain. Using the device detected intervals, the discrimination algorithm identified 16 FPs, which translates to a 19% reduction in FPs and a 6% improvement in PPV from 38% to 44%.

Implantable Medical Device

Figure 6A:
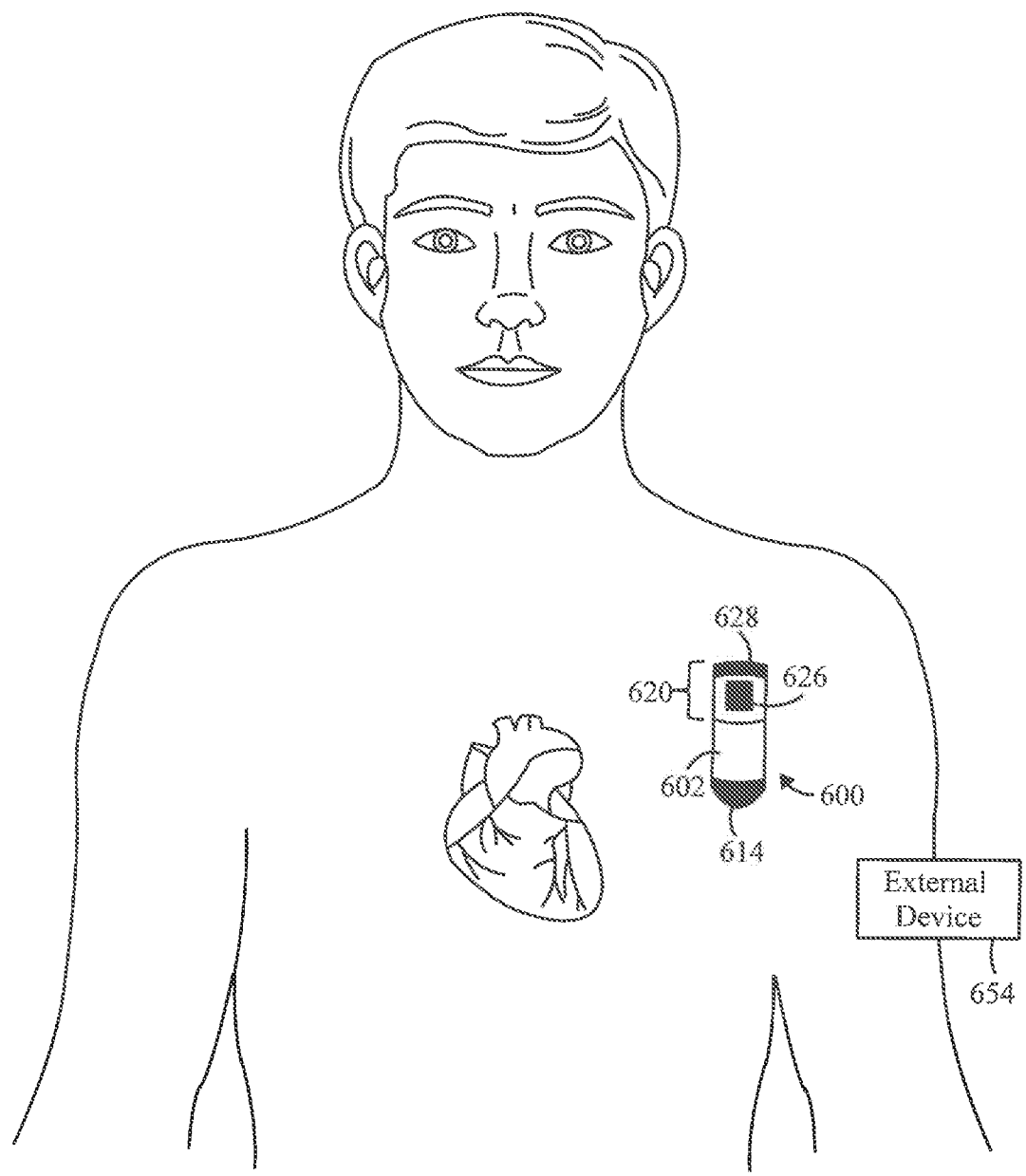
FIG. 6A illustrates an implantable cardiac monitoring device (ICM) intended for subcutaneous implantation at a site near the heart.

FIG. 6A illustrates an implantable cardiac monitoring device (ICM) 600 intended for subcutaneous implantation at a site near the heart. The ICM 600 includes a pair of spaced-apart sense electrodes 614, 626 positioned with respect to a housing 602. The sense electrodes 614, 626 provide for detection of far field electrogram signals. Numerous configurations of electrode arrangements are possible. For example, the electrode 614 may be located on a distal end of the ICM 600, while the electrode 626 is located on a proximal side of the ICM 600. Additionally or alternatively, electrodes 626 may be located on opposite sides of the ICM 600, opposite ends or elsewhere. The distal electrode 614 may be formed as part of the housing 602, for example, by coating all but a portion of the housing with a nonconductive material such that the uncoated portion forms the electrode 614. In this case, the electrode 626 may be electrically isolated from the housing 602 electrode by placing it on a component separate from the housing 602, such as the header 620. Optionally, the header 620 may be formed as an integral portion of the housing 602. The header 620 includes an antenna 628 and the electrode 626. The antenna 628 is configured to wirelessly communicate with an external device 654 in accordance with one or more predetermined wireless protocols (e.g., Bluetooth, Bluetooth low energy, Wi-Fi, etc.). The housing 602 includes various other components such as: sense electronics for receiving signals from the electrodes, a microprocessor for processing the signals in accordance with algorithms, such as the AF detection algorithm described herein, a loop memory for temporary storage of CA data, a device memory for long-term storage of CA data upon certain triggering events, such as AF detection, sensors for detecting patient activity and a battery 672 for powering components.

In at least some embodiments, the ICM 600 is configured to be placed subcutaneously utilizing a minimally invasive approach. Subcutaneous electrodes are provided on the housing 602 to simplify the implant procedure and eliminate a need for a transvenous lead system. The sensing electrodes may be located on opposite sides of the device and designed to provide robust episode detection through consistent contact at a sensor-tissue interface. The ICM 600 may be configured to be activated by the patient or automatically activated, in connection with recording subcutaneous ECG signals.

The ICM 600 senses far field, subcutaneous CA signals, processes the CA signals to detect arrhythmias and if an arrhythmia is detected, automatically records the CA signals in memory for subsequent transmission to an external device 654. The CA signal processing and AF detection is provided for, at least in part, by algorithms embodied in or implemented by the microprocessor. The ICM 600 includes one or more processors and memory that stores program instructions directing the processors to implement AF detection utilizing an on-board R-R interval irregularity (ORI) process that analyzes cardiac activity signals collected over one or more sensing channels.

Figure 6B:
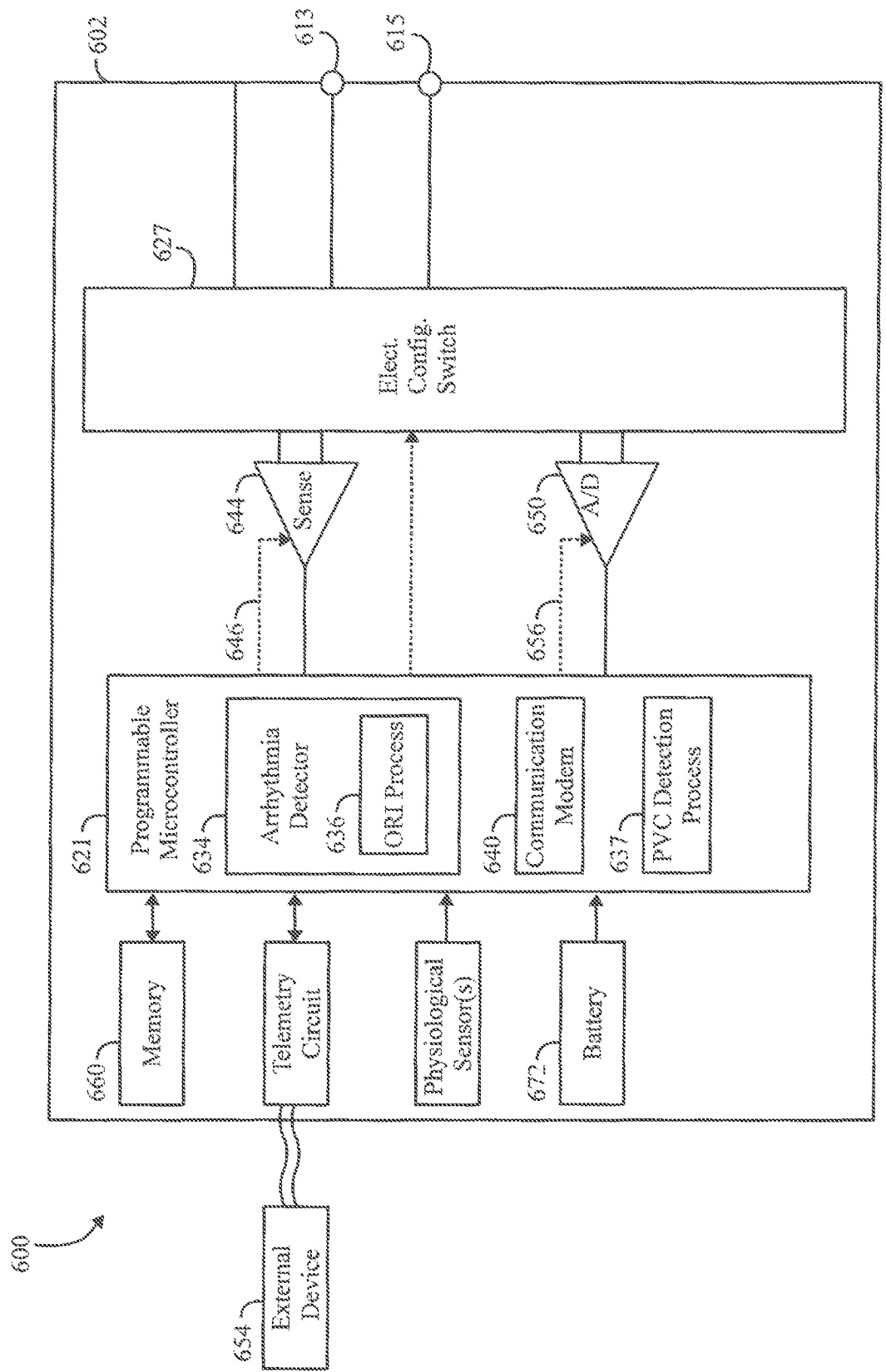
FIG. 6B shows a block diagram of the ICM 600 formed in accordance with embodiments herein.

FIG. 6B shows a block diagram of the ICM 600 formed in accordance with embodiments herein. The ICM 600 may be implemented to monitor ventricular activity alone, or both ventricular and atrial activity through sensing circuitry. The ICM 600 has a housing 602 to hold the electronic/computing components. The housing 602 (which is often referred to as the "can", "case", "encasing", or "case electrode") may be programmably selected to act as an electrode for certain sensing modes. Housing 602 further includes a connector (not shown) with at least one terminal 613 and optionally additional terminals 615. The terminals 613, 615 may be coupled to sensing electrodes that are provided upon or immediately adjacent the housing 602. Optionally, more than two terminals 613, 615 may be provided in order to support more than two sensing electrodes, such as for a bipolar sensing scheme that uses the housing 602 as a reference electrode. Additionally or alternatively, the terminals 613, 615 may be connected to one or more leads having one or more electrodes provided thereon, where the electrodes are located in various locations about the heart. The type and location of each electrode may vary.

The ICM 600 includes a programmable microcontroller 621 that controls various operations of the ICM 600, including cardiac monitoring. Microcontroller 621 includes a microprocessor (or equivalent control circuitry), RAM and/or ROM memory, logic and timing circuitry, state machine circuitry, and I/O circuitry. The microcontroller 621 also performs the operations described herein in connection with collecting cardiac activity data and analyzing the cardiac activity data to identify AF episodes.

A switch 627 is optionally provided to avow selection of different electrode configurations under the control of the microcontroller 621. The electrode configuration switch 627 may include multiple switches for connecting the desired electrodes to the appropriate I/O circuits, thereby facilitating electrode programmability. The switch 627 is controlled by a control signal 646 from the microcontroller 621. Optionally, the switch 627 may be omitted and the I/O circuits directly connected to the housing electrode 614 and a second electrode 626. Microcontroller 621 includes an arrhythmia detector 634 that is configured to analyze cardiac activity signals to identify potential AF episodes as well as other arrhythmias (e.g., Tachycardias, Bradycardias, Asystole, etc.). By way of example, the arrhythmia detector 634 may implement an AF detection algorithm as described in U.S. Pat. No. 8,135,456, the complete subject matter of which is incorporated herein by reference. Although not shown, the microcontroller 621 may further include other dedicated circuitry and/or firmware/software components that assist in monitoring various conditions of the patient's heart and managing pacing therapies.

The ICM 600 is further equipped with a communication modem (modulator/demodulator) 640 to enable wireless communication. In one implementation, the communication modem 640 uses high frequency modulation, for example using RF, Bluetooth or Bluetooth Low Energy telemetry protocols. The signals are transmitted in a high frequency range and will travel through the body tissue in fluids without stimulating the heart or being felt by the patient. The communication modem 640 may be implemented in hardware as part of the microcontroller 621, or as software/firmware instructions programmed into and executed by the microcontroller 621. Alternatively, the modem 640 may reside separately from the microcontroller as a standalone component. The modem 640 facilitates data retrieval from a remote monitoring network. The modem 640 enables timely and accurate data transfer directly from the patient to an electronic device utilized by a physician.

The ICM 600 includes sensing circuitry 644 selectively coupled to one or more electrodes that perform sensing operations, through the switch 627 to detect cardiac activity data indicative of cardiac activity. The sensing circuitry 644 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the features of interest. In one embodiment, switch 627 may be used to determine the sensing polarity of the cardiac signal by selectively closing the appropriate switches.

The output of the sensing circuitry 644 is connected to the microcontroller 621 which, in turn, determines when to store the cardiac activity data of CA signals (digitized by the A/D data acquisition system 650) in the memory 660. For example, the microcontroller 621 may only store the cardiac activity data (from the A/D data acquisition system 650) in the memory 660 when a potential AF episode is detected. The sensing circuity 644 receives a control signal 646 from the microcontroller 621 for purposes of controlling the gain, threshold, polarization charge removal circuitry (not shown), and the timing of any blocking circuitry (not shown) coupled to the inputs of the sensing circuitry.

In the example of FIG. 6B, a single sensing circuitry 644 is illustrated. Optionally, the ICM 600 may include multiple sensing circuitries, similar to sensing circuitry 644, where each sensing circuitry is coupled to two or more electrodes and controlled by the microcontroller 621 to sense electrical activity detected at the corresponding two or more electrodes. The sensing circuitry 644 may operate in a unipolar sensing configuration or in a bipolar sensing configuration. Optionally, the sensing circuitry 644 may be removed entirely and the microcontroller 621 perform the operations described herein based upon the CA signals 656 from the A/D data acquisition system 650 directly coupled to the electrodes.

The arrhythmia detector 634 of the microcontroller 621 includes an onboard R-R interval irregularity (ORI) process 636 that detects AF episodes using an automatic detection algorithm that monitors for irregular ventricular rhythms that are commonly known to occur during AF. The ORI process 636 may be implemented as firmware, software and/or circuits. The ORI process 636 uses a hidden Markov Chains and Euclidian distance calculations of similarity to assess the transitionary behavior of one R-wave (RR) interval to another and compare the patient's RR interval transitions to the known RR interval transitions during AF and non-AF episodes obtained from the same patient and/or many patients. The ORI process 636 detects AF episodes over a short number of RR intervals. For example, the ORI process 636 may implement the AF detection methods described in U.S. Pat. No. 8,135,456, the complete subject matter of which is incorporated herein by reference in its entirety.

The microcontroller 621 further includes include a PVC detection module 637 configured to implement one or more of the operations discussed herein. By way of example, the PVC detection module 637 may represent one or more processors that, when executing the program instructions, are configured to: calculate a distribution characteristic for the cardiac beats, from the series of cardiac beats, that exhibit a first transition type from the set of transition types; calculate a discrimination score based on the distribution characteristic of the cardiac beats across the CL distribution metric; and designating the CA signals to include a predetermined level of PVC burden based on the discrimination score. Additionally or alternatively, the PVC detection module 637 may be further configured to build the CL distribution metric by: obtaining cardiac activity (CA) signals for a series of cardiac beats; determining ventricular cycle lengths (CL) for the series of cardiac beats from the CA signals; determining difference combinations between consecutive CLs for corresponding sets of the cardiac beats; and plotting the comparison between the combinations of the RRI difference pairs onto a Lorentz plot coordinate system. The PVC detection module 637 may build the CL distribution metric by plotting, along a first axis, the differences between consecutive RR intervals for each beat, and, by plotting along a second axis, differences between consecutive RR intervals for each subsequent beat. The PVC detection module 637 may be further configured to calculate a normalization for the distribution characteristic of the cardiac beats exhibiting the first transition type. The first transition type represents long-short ΔRRI transitions and the distribution characteristic corresponds to variance of the cardiac beats exhibiting the long-short ΔRRI transitions. The normalization represents a normalization between the variance of the cardiac beats exhibiting the long-short ΔRRI transitions and a variance of at least a portion of the cardiac beats associated with one or more of the transition types from the set of transition types. As explained herein. CL distribution metric represents a Lorentz plot of the cardiac beats, the method further comprising normalizing the distribution characteristic for the cardiac beats that exhibit the first transition type by calculating a normalization represents a normalization between i) a variance of the cardiac beats in quadrant IV in the Lorentz plot and ii) a variance of cardiac beats in quadrants I-IV in the Lorentz plot, wherein the discrimination score is calculated based on the normalization. The PVC detection module 637 may be configured to calculate the discrimination score by determining a first relation between: i) a second relation between the cardiac beats exhibiting the first transition type and cardiac beats exhibiting a second transition type from the set of transition types; and ii) the distribution characteristic, for the cardiac; beats exhibiting the first transition type. The PVC detection module 637 may be configured to calculate the second relation by calculating a second ratio of a number of cardiac beats exhibiting the first transition type and a number of cardiac beats exhibiting the second transition type, the first relation representing a first ratio between the first ratio and a normalization of the distribution characteristic.

Optionally, the PVC detection module 637 may be implemented by one or more processors that are housed within at least one of an implantable medical device, an implantable cardiac monitor, a local external device, or a remote server.

Subcutaneous Implantable Medical Device

Figure 6C:
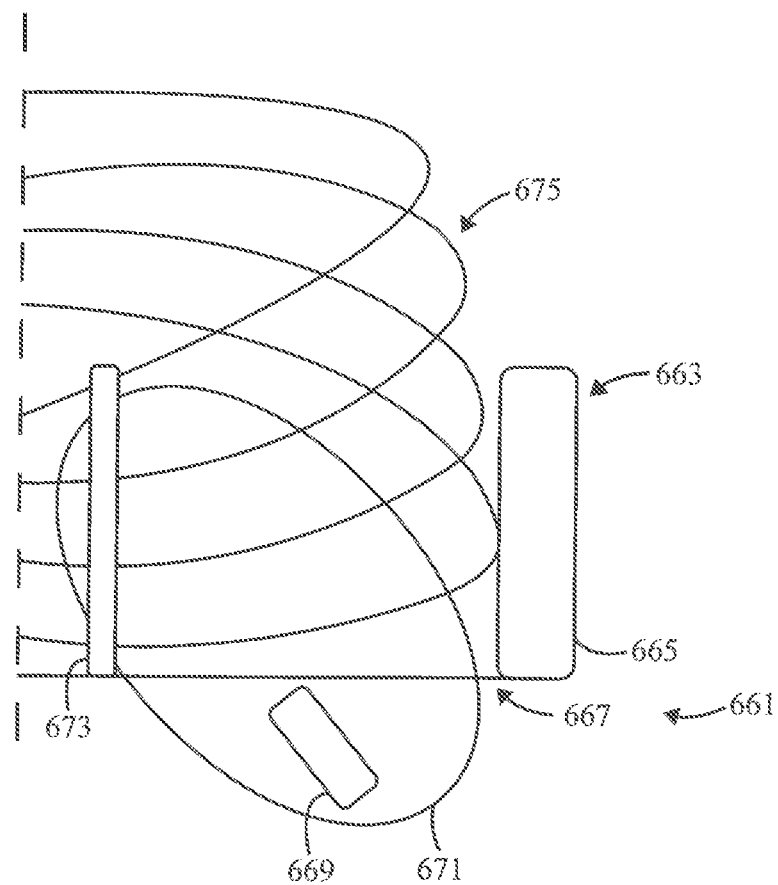
FIG. 6C illustrates a graphical representation of an implantable medical system that is configured to operate in accordance with embodiments herein.

FIG. 6C illustrates a graphical representation of an implantable medical system that is configured to operate in accordance with embodiments herein. Embodiments may be implemented in connection with one or more subcutaneous implantable medical devices (S-IMDs). Non-limiting examples of S-IMDs include one or more of subcutaneous implantable cardioverter defibrillators (S-ICD). For example, the S-IMD may include one or more structural and/or functional aspects of the device(s) described in U.S. application Ser. No. 15/973,219, titled "IMPLANTABLE MEDICAL SYSTEMS AND METHODS INCLUDING PULSE GENERATORS AND LEADS", filed May 7, 2018; U.S. application Ser. No. 15/973,195, titled "SUBCUTANEOUS IMPLANTATION MEDICAL DEVICE WITH MULTIPLE PARASTERNAL-ANTERIOR ELECTRODES", filed May 7, 2018; which are hereby incorporated by reference in their entireties.

The system 661 includes a subcutaneous implantable medical device (S-IMD) 663 that is configured to be implanted in a subcutaneous area exterior to the heart. The S-IMD 663 is positioned in a subcutaneous area or region, and more particularly in a mid-axillary position along a portion of the rib cage 675. Optionally, the system 661 may also include a leadless pacemaker 669 implanted within the heart, such as at an apex 671 of the right ventricle. Optionally, the leadless pacemaker 669 may be omitted entirely. The system 661 does not require insertion of a transvenous lead.

The pulse generator 665 may be implanted subcutaneously and at least a portion of the lead 667 may be implanted subcutaneously. In particular embodiments, the S-IMD 663 is an entirely or fully subcutaneous S-IMD. Optionally, the S-IMD 663 may be positioned in a different subcutaneous region.

The S-IMD 663 includes a pulse generator 666 and at least one lead that is operably coupled to the pulse generator 665. The lead 667 includes at least one electrode segment 673 that is used for providing MV shocks for defibrillation. Optionally, the lead 667 may include one or more sensing electrodes. The pulse generator 665 includes a housing that forms or constitutes an electrode utilized to deliver MV shocks. The electrode associated with the housing of the pulse generator 665 is referred to as the "CAN" electrode.

In an alternative embodiment, the lead 667 may include one or more electrode segments, in which the electrode segments are spaced apart from one another having an electrical gap therebetween. The lead body may extend between the gap. One electrode segment may be positioned along an anterior of the chest, while another electrode segment may be positioned along a lateral and/or posterior region of the patient. The electrode segments may be portions of the same lead, or the electrode segments may be portions of different leads. The electrode segments may be positioned subcutaneously at a level that aligns with the heart of the patient for providing a sufficient amount of energy for defibrillation. The lead includes a lead body that extends from the mid-auxiliary position along an inter-costal area between ribs and oriented with the coil electrode(s) extending along the sternum (e.g., over the sternum or parasternally within one to three centimeters from the sternum). A proximal end the coil electrodes may be located proximate to the xiphoid process.

Closing Statements

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and Illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the Figures, which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein," Moreover, in the following claims, the terms "first," "second," and "third," etc. are used merely as labels, and are not intended to impose numerical requirements on their objects or order of execution on their acts.

What is claimed is:

1. A computer implemented method comprising:
   under control of one or more processors of an implantable medical device (IMD) configured with specific executable instructions,
   collecting, via sensing circuitry of the IMD, cardiac activity (CA) signals for a series of cardiac beats of a patient in which the IMD is implanted;
   determining R-R interval (RRI) difference pairs for the series of cardiac beats based on the CA signals;
   generating a cycle length (CL) distribution metric that plots the cardiac beats into four quadrants corresponding to transition types, wherein data points of the CL distribution metric are based on combinations of consecutive RRI difference pairs of the RRI difference pairs;
   calculating a distribution characteristic for the cardiac beats, from the series of cardiac beats, that exhibit a long-short transition type of the transition types in the CL distribution metric, the distribution characteristic representing a measure of an extent to which the cardiac beats are spread across quadrant IV of the quadrants which corresponds to the long-short transition type;

calculating a discrimination score based on the distribution characteristic of the cardiac beats across the CL distribution metric, wherein the discrimination score is calculated by dividing i) a ratio between a number of the data points in the quadrant IV corresponding to the long-short transition type and a number of the data points in quadrant I of the CL distribution metric corresponding to a long-long transition type of the transition types, by ii) a normalization of the distribution characteristic; and delivering, via a pulse generator, stimulation pulses for atrial fibrillation (AF) therapy based on a comparison of the discrimination score to a score threshold which indicates that no premature ventricular contractions (PVCs) are detected.

2. The method of claim 1, wherein determining the RRI difference pairs comprises:

determining ventricular cycle lengths for the series of cardiac beats from the CA signals; and determining the RRI difference pairs between consecutive pairs of the ventricular cycle lengths for corresponding sets of successive cardiac beats in the series, and wherein generating the CL distribution metric comprises plotting the combinations of the consecutive RRI difference pairs onto a Lorenz plot coordinate system.

3. The method of claim 1, wherein generating the CL distribution metric comprises plotting, along a first axis, differences between consecutive RRIs for a set of the cardiac beats, and plotting, along a second axis, differences between consecutive RRIs for a subsequent set of the cardiac beats.

4. The method of claim 1, wherein the distribution characteristic corresponds to a Q4 variance of the cardiac beats in the quadrant IV of the CL distribution metric corresponding to the long-short transition type, the Q4 variance independent of a variance of the cardiac beats in the other three quadrants of the CL distribution metric.

5. The method of claim 1, wherein the normalization of the distribution characteristic represents a normalization between a variance of the cardiac beats in the quadrant IV exhibiting the long-short transition type and a variance of the cardiac beats in one or more of the other three quadrants exhibiting other corresponding transition types of the transition types.

6. The method of claim 5, wherein the normalization is a ratio between the variance of the cardiac beats in the quadrant IV and the variance of the cardiac beats in all four quadrants of the CL distribution metric.

7. The method of claim 1, further comprising designating the series of cardiac beats to include a predetermined level of PVC burden based on the discrimination score, and saving the predetermined level of PVC burden.

8. The method of claim 1, wherein the IMD includes the pulse generator.

9. The method of claim 1, wherein, based on a comparison of the discrimination score to a score threshold indicating that PVCs are detected, the method comprises resetting an atrial fibrillation (AF) count buffer.

10. An implantable medical device (IMD) comprising:

sensing circuitry configured to collect cardiac activity (CA) signals for a series of cardiac beats of a patient in which the IMD is implanted;

a memory configured to store program instructions; and one or more processors that, when executing the program instructions, are configured to:

determine R-R interval (RRI) difference pairs for the series of cardiac beats based on the CA signals;

generate a cycle length (CL) distribution metric that plots the cardiac beats into four quadrants corresponding to transition types, wherein data points of the CL distribution metric are based on combinations of consecutive RRI difference pairs of the RRI difference pairs;

calculate a distribution characteristic for the cardiac beats, from the series of cardiac beats, that exhibit a long-short transition type of the transition types in the CL distribution metric, the distribution characteristic representing a measure of an extent to which the cardiac beats are spread across quadrant IV of the quadrants which corresponds to the long-short transition type;

calculate a discrimination score based on the distribution characteristic of the cardiac beats across the CL distribution metric, wherein the one or more processors are configured to calculate the discrimination score by dividing i) a ratio between a number of the data points in the quadrant IV corresponding to the long-short transition type and a number of the data points in quadrant I of the CL distribution metric corresponding to a long-long transition type of the transition types, by ii) a normalization of the distribution characteristic; and deliver, via a pulse generator, stimulation pulses for atrial fibrillation (AF) therapy based on a comparison of the discrimination score to a score threshold which indicates that no premature ventricular contractions (PVCs) are detected.

11. The IMD of claim 10, wherein the one or more processors are configured to determine the RRI difference pairs by:

determining ventricular cycle lengths for the series of cardiac beats from the CA signals; and determining the RRI difference pairs between consecutive pairs of the ventricular cycle lengths for corresponding sets of successive cardiac beats in the series, and wherein the one or more processors are configured to generate the CL distribution metric by plotting the combinations of the consecutive RRI difference pairs onto a Lorenz plot coordinate system.

12. The IMD of claim 10, wherein the one or more processors are configured to generate the CL distribution metric by plotting, along a first axis, differences between consecutive RRIs for a set of the cardiac beats, and plotting, along a second axis, differences between consecutive RRIs for a subsequent set of the cardiac beats.

13. The IMD of claim 10, wherein the distribution characteristic corresponds to a Q4 variance of the cardiac beats in the quadrant IV of the CL distribution metric corresponding to the long-short transition type, the Q4 variance independent of a variance of the cardiac beats in the other three quadrants of the CL distribution metric.

14. The IMD of claim 10, wherein the normalization of the distribution characteristic represents a normalization between a variance of the cardiac beats in the quadrant IV exhibiting the long-short transition type and a variance of the cardiac beats in one or more of the other three quadrants exhibiting other corresponding transition types of the transition types.

15. The IMD of claim 10, wherein the normalization is a ratio between the variance of the cardiac beats in the quadrant IV and the variance of the cardiac beats in all four quadrants of the CL distribution metric.

16. The IMD of claim 10, wherein the implantable medical device is an implantable cardiac monitor.

17. The IMD of claim 10, wherein the IMD includes the pulse generator.

18. The IMD of claim 10, wherein the one or more processors are configured to reset an atrial fibrillation (AF) count buffer based on a comparison of the discrimination score to a score threshold indicating that PVCs are detected.

* * * * *